(12) United States Patent
Kottler et al.

(10) Patent No.: US 7,924,973 B2
(45) Date of Patent: Apr. 12, 2011

(54) INTERFEROMETER DEVICE AND METHOD

(75) Inventors: Christian Kottler, Zurich (CH); Rolf Kaufmann, Zurich (CH)

(73) Assignee: Csem Centre Suisse D'Electronique Et De Microtechnique SA, Neuchatel (CH)

( * ) Notice: Subject to any disclaimer, the term of this patent is extended or adjusted under 35 U.S.C. 154(b) by 358 days.

(21) Appl. No.: 12/269,449

(22) Filed: Nov. 12, 2008

(65) Prior Publication Data

US 2009/0128830 A1    May 21, 2009

Related U.S. Application Data

(60) Provisional application No. 60/988,278, filed on Nov. 15, 2007.

(51) Int. Cl.
*G03H 5/00* (2006.01)
*G01T 1/36* (2006.01)
(52) U.S. Cl. ............................................. 378/36; 378/82
(58) Field of Classification Search .................. 378/36, 378/62, 82, 145; 356/521, 497, 479
See application file for complete search history.

(56) References Cited

U.S. PATENT DOCUMENTS

| | | | | |
|---|---|---|---|---|
| 5,812,629 A * | 9/1998 | Clauser | ............................ | 378/62 |
| 6,804,324 B2 * | 10/2004 | Martynov et al. | ................. | 378/36 |
| 7,639,786 B2 * | 12/2009 | Baumann et al. | .............. | 378/145 |
| 2005/0190882 A1 | 9/2005 | McGuire | | |
| 2005/0286680 A1 * | 12/2005 | Momose | .......................... | 378/62 |
| 2007/0183581 A1 * | 8/2007 | Heismann et al. | ............. | 378/145 |

FOREIGN PATENT DOCUMENTS

| | | |
|---|---|---|
| EP | 1 623671 A1 | 2/2006 |
| EP | 1731099 A1 | 12/2006 |
| WO | WO2004/071298 A1 | 8/2004 |
| WO | WO2007/074029 A1 | 7/2007 |

OTHER PUBLICATIONS

Pfeiffer et al, "Hard X-Ray Phase Tomography With Low-Brilliance Sources", Phys. Rev. Lett. 98, pp. 108105-1-108105-4, The American Physical Society.
Pfeiffer et al, "Phase retrieval and differential phase-contrast imaging with low-brilliance X-ray sources", pp. 258-261, 2006, Nature Publishing Group.

* cited by examiner

*Primary Examiner* — Irakli Kiknadze
(74) *Attorney, Agent, or Firm* — Martin Fleit; Paul D. Bianco; Fleit Gibbons Gutman Bongini & Bianco PL

(57) ABSTRACT

The present invention discloses an interferometer device and method. In embodiments, the device comprises an electromagnetic radiation source emitting radiation having a first mean wavelength $\lambda_{LE}$; a phase grating having a first aspect ratio; an absorption grating having a second aspect ratio; and a detector. The electromagnetic radiation source, the phase grating, the absorption grating and the detector are radiatively coupled with each other. The absorption grating is positioned between the detector and the phase grating; the electromagnetic radiation source is positioned in front of the source grating; and wherein the phase grating is designed such to cause a phase shift that is smaller than $\pi$ on the emitted radiation. Additional and alternative embodiments are specified and claimed.

14 Claims, 12 Drawing Sheets

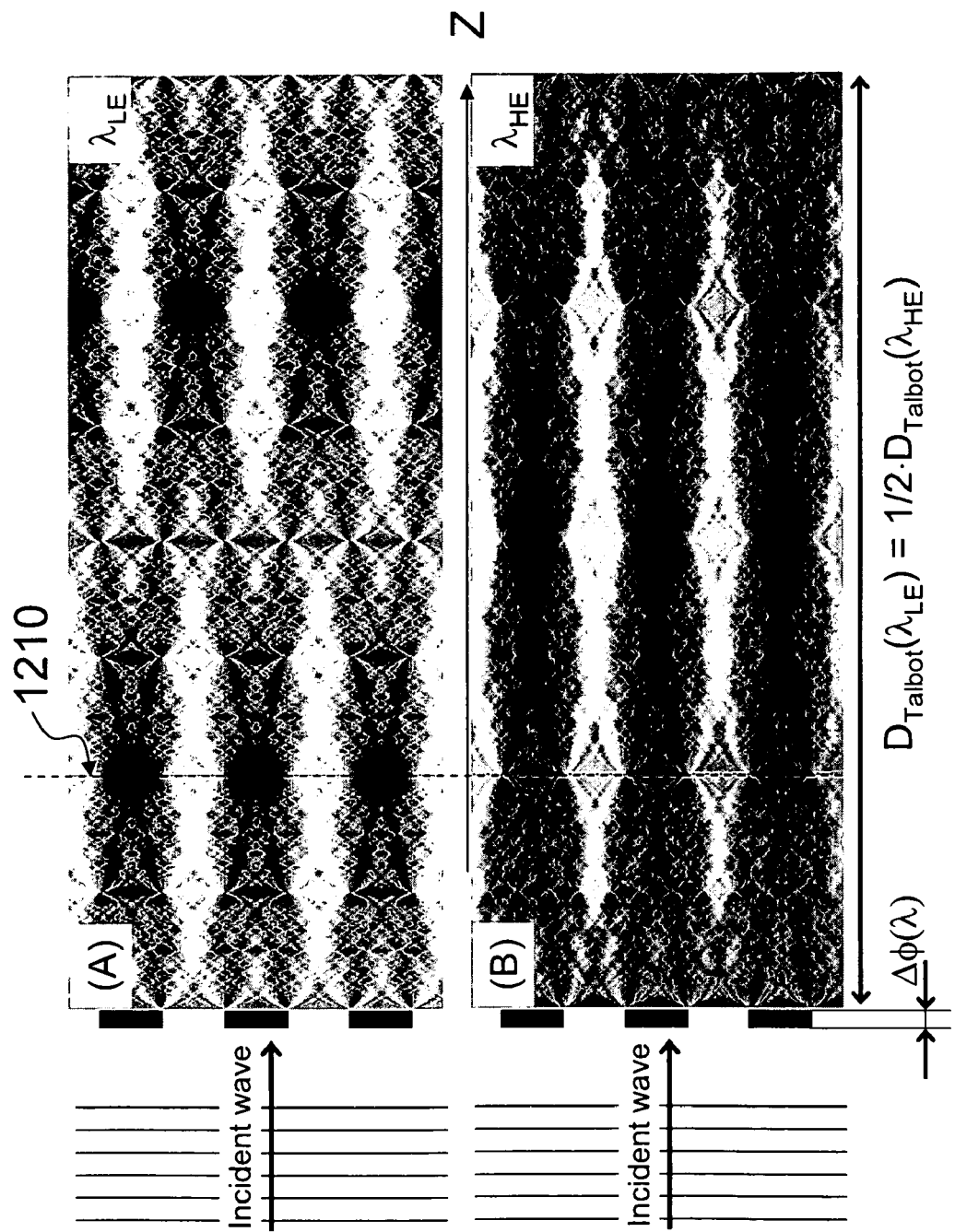

INTERFEROMETER DEVICE AND METHOD

CROSS-REFERENCE TO RELATED APPLICATIONS

This patent application claims priority from U.S. Provisional Patent Application No. 60/988,278 filed on Nov. 15, 2007, the disclosure of which is incorporated herein by reference in its entirety.

FIELD OF THE INVENTION

This invention relates to imaging devices and methods, and more particularly, to imaging devices and methods accomplished with interferometers.

BRIEF DESCRIPTION OF THE DRAWINGS

These and further features and advantages of the invention will become more clearly understood in the light of the ensuing description of embodiments thereof, given by way of example only, with reference to the accompanying figures, wherein:

FIG. 12A is a schematic illustration of amplitude interference patterns obtained from illumination of a pure phase grating with a low energy (LE) plane wave, wherein the phase grating is designed such that the relative phase shift caused on the incident LE wave suffers $\Delta\phi(\lambda_{LE}) = \pi/2$, according to an embodiment of the invention; and FIG. 12B is a schematic illustration of amplitude interference patterns obtained from illumination of a pure phase grating with a high energy (HE) plane wave, wherein $\lambda_{HE} = \frac{1}{2} \lambda_{LE}$, and wherein the phase grating is designed such that the relative phase shift caused on the incident HE wave suffers $\Delta\phi(\lambda_{HE}) = \pi/4$, according to an embodiment of the invention.

Where considered appropriate, reference numerals may be repeated among the figures to indicate identical elements but may not be referenced in the description for all figures.

BACKGROUND OF THE INVENTION

Figure 1B:
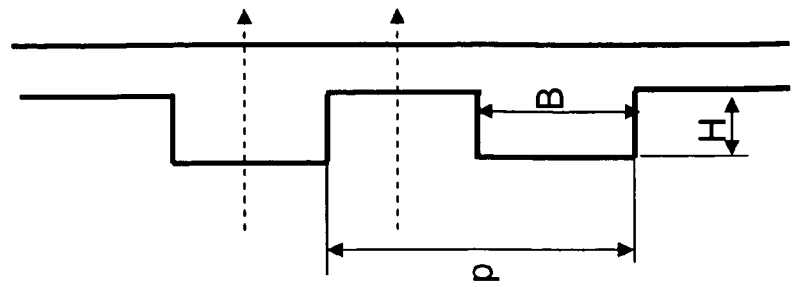
FIG. 1B is a schematic illustration of a grating.

X-ray imaging is of high importance in view of its numerous applications such as, for example, security screening, medical imaging, quality inspection and non-destructive testing. With growing need for better resolution, accuracy, and improved frame rate of the generated X-ray image sequence, various techniques have been employed thus far including X-ray imaging interferometry and dual-energy radiography.

Publications concerning interferometry techniques are listed below. Patent application EP1731099, entitled "Interferometer for quantitative phase contrast imaging and tomography with an incoherent polychromatic x-ray source" discloses an x-ray interferometer arrangement comprising only one phase grating (122) and absorption grating (123). This interferometer can be used to obtain phase contrast images with a standard x-ray tube. Additionally, the new type of interferometer may use a source consisting of an array of individual sub-sources. Each of the sub-sources is individually coherent but mutually incoherent to the other sub-sources. The array of sub-sources may be generated by placing an array of slits, i.e. an additional amplitude grating (121) close to the source.

Pfeiffer et al. show in the article entitled "Hard x-ray phase tomography with low-brilliance sources", published in Phys. Rev. Lett. 98, 108105 (2007), that a setup consisting of three transmission gratings together with appropriate tomographic filtered back projection (FBP) algorithms can yield quantitative 3D information of the real and imaginary part of the refractive index distribution of macroscopic objects. The setup can be used with conventional X-ray tube sources with square millimetre source sizes and several kW power.

Pfeiffer et al. disclose in the article entitled "Phase retrieval and differential phase-contrast imaging with low-brilliance X-ray source", published in Nature Physics 2, 258-261 (2006), a setup consisting of three transmission gratings can efficiently yield quantitative differential phase-contrast images with conventional X-ray tubes. In contrast with existing techniques, the method requires no temporal coherence, is mechanically robust, and can be scaled up to large fields of view.

Patent application WO2007074029, entitled "Focus detector arrangement for generating phase-contrast x-ray images and method for this", discloses a focus detector arrangement of an X-ray apparatus for generating projective or tomographic phase-contrast images of an examination object, wherein a bundle of spatially coherent X-rays is generated by an anode that has areas of different radiation emission arranged in strips and extending parallel to the grid lines of the phase grid of the focus detector arrangement. In addition, the invention also relates to a method for generating projective or tomographic X-ray phase-contrast images of an examination object with the aid of such a focus detector arrangement, wherein a bundle of coherent radiation is generated by an anode that has areas of different radiation emission arranged in strips and extending parallel to the grid lines of the phase grid.

Patent application WO2004071298, entitled "Apparatus And Method To Obtain Phase Contrast X-Ray Images" discloses an apparatus for generating a phase contrast x-ray image comprising in an optical path as seen in the direction of the light flow: a) an incoherent x-ray source; b) a first beam splitter grating for splitting the light beams of said x-ray source; c) a second beam recombiner grating for recombining the splitted beams in a recombination distance from the second beam recombiner grating; d) an optional third analyzer grating in order to offer an adsorption lines grating matching the interference lines downstream of said second beam recombiner grating in an analyzer plane (a); e) an image detector disposed downstream of the analyzer plane (a); and f) a means for introducing a sample into said optical path upstream or downstream of the second beam recombiner grating.

Patent application EP1623671, entitled "X-Ray Imaging System and Imaging Method", discloses an X-ray imaging apparatus equipped with first and second diffraction gratings and an X-ray image detector. The first diffraction grating is constructed to generate the Talbot effect in the X-rays diffracted by the first diffraction grating. The second diffraction grating is configured so as to diffract the X-rays diffracted by the first diffraction grating. The X-ray image detector is configured so as to detect the X-rays diffracted by the second diffraction grating. By diffracting X-rays diffracted by the first diffraction grating, the second diffraction grating is capable of forming image contrast caused by changes in phase of X-rays due to the subject arranged in front of the first diffraction grating or between the first diffraction grating and the second diffraction grating. The X-ray image detector is capable of detecting X-rays creating image contrast.

Figure 1A:
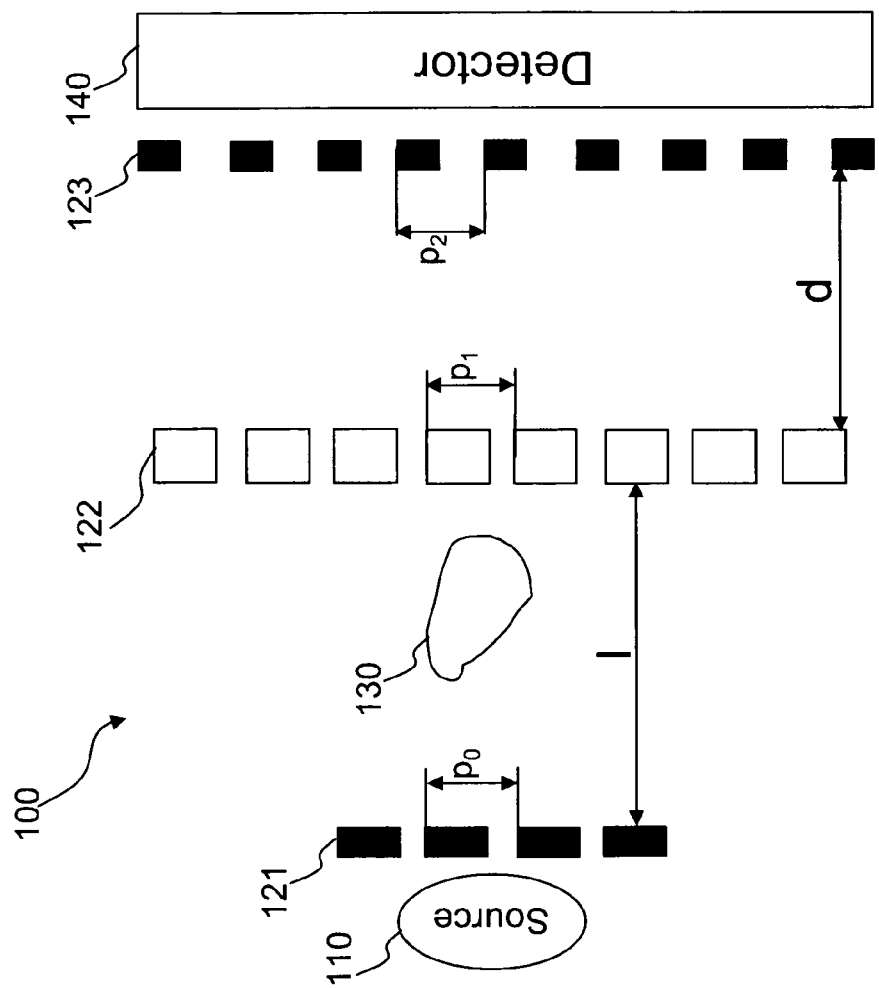
FIG. 1A is a schematic illustration of a setup of an interferometer device.
Figure 2:
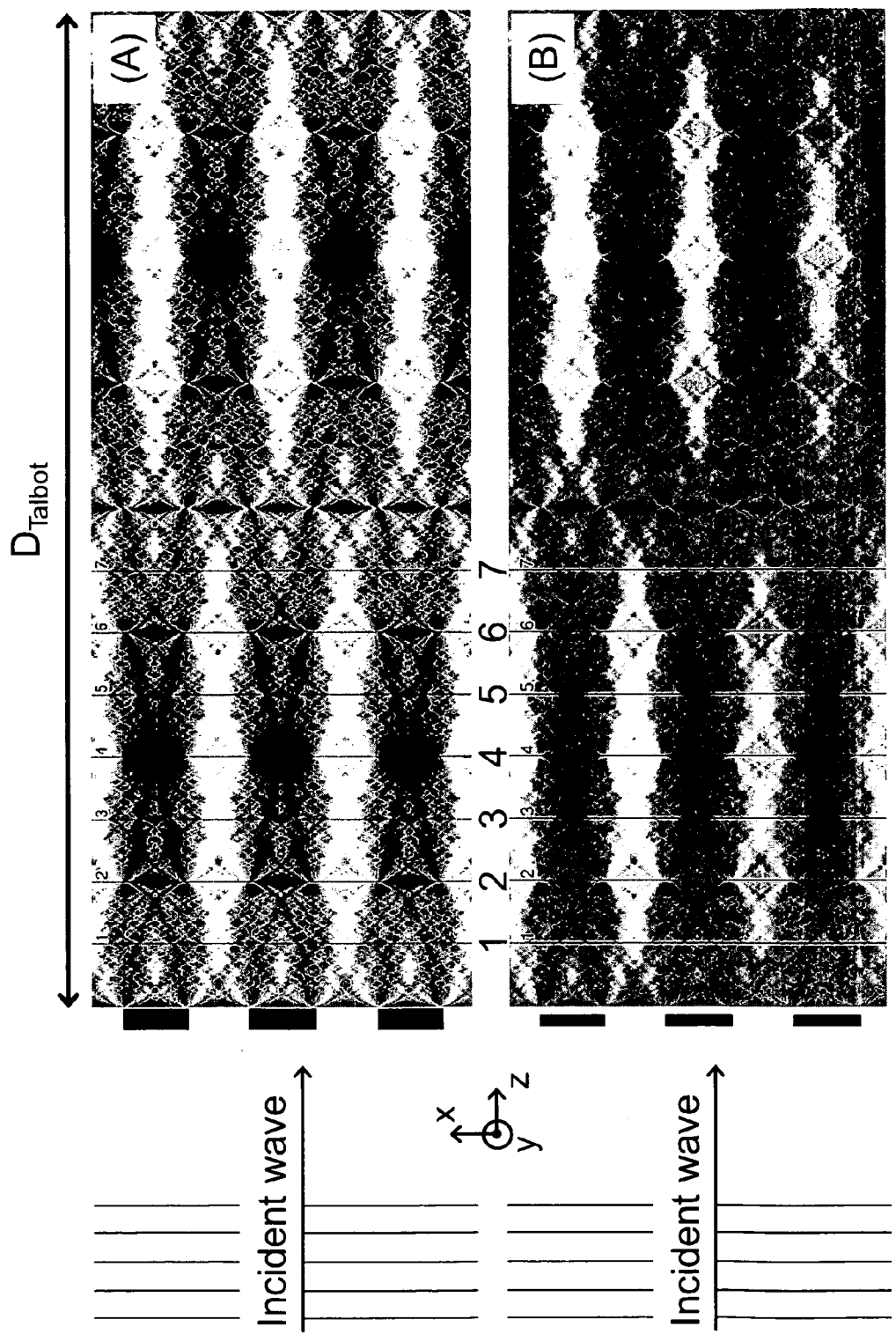
FIG. 2A is a schematic illustration of amplitude interference patterns for a phase grating designed to cause a phase shift of $\Delta\phi < \pi/2$, according to an embodiment of the invention.
FIG. 2B is a schematic illustration of amplitude interference patterns for a phase grating designed to cause on a monochromatic radiation a phase shift of $\Delta\phi = \pi/4$, according to an embodiment of the invention.
Figure 3A:
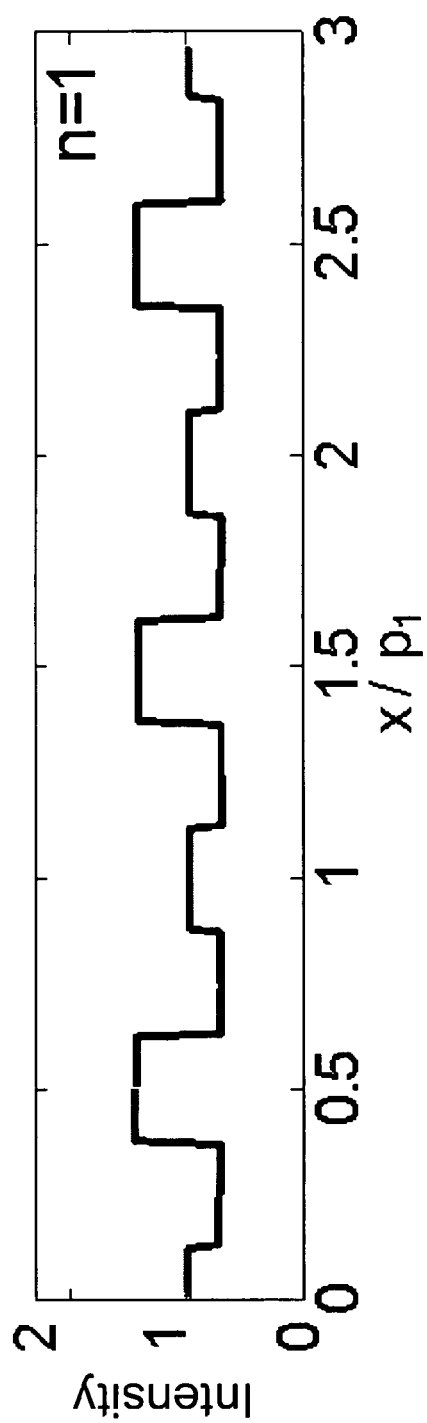
FIG. 3A is a schematic illustration of intensity profiles corresponding to transverse cross-sections for fractional Talbot order n=1 of the interference pattern of FIG. 2A.
Figure 3B:
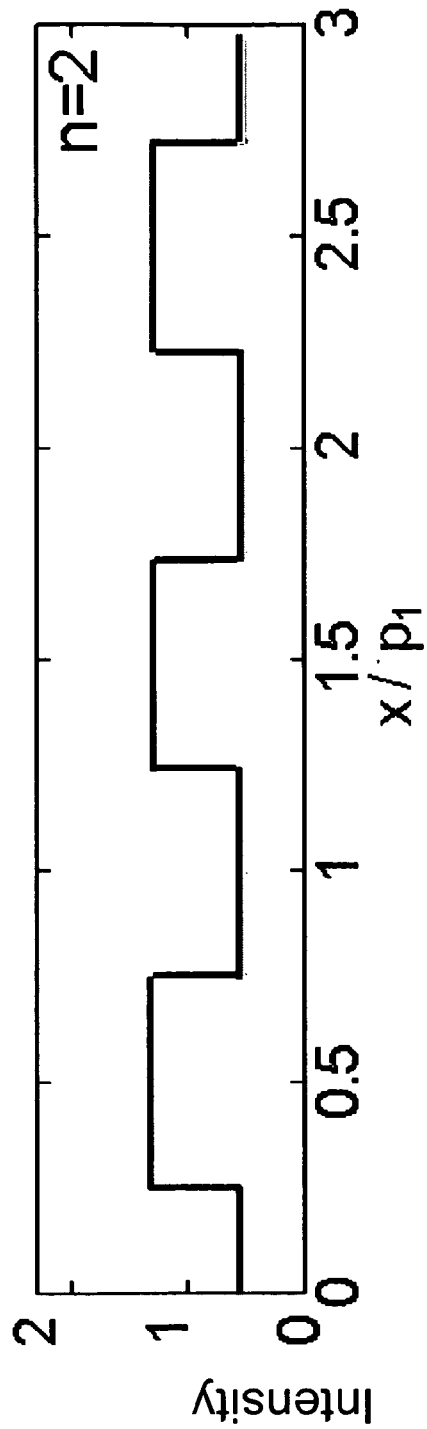
FIG. 3B is a schematic illustration of intensity profiles corresponding to transverse cross-sections for fractional Talbot order n=2 of the interference pattern of FIG. 2A.
Figure 4A:
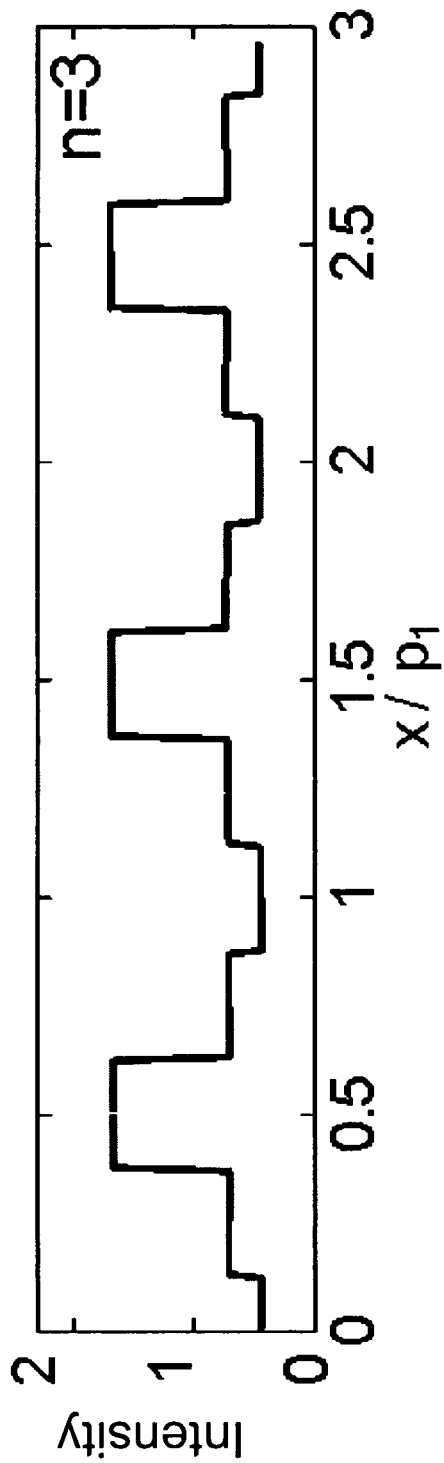
FIG. 4A is a schematic illustration of intensity profiles corresponding to transverse cross-sections for fractional Talbot order n=3 of the interference pattern of FIG. 2A.
Figure 4B:
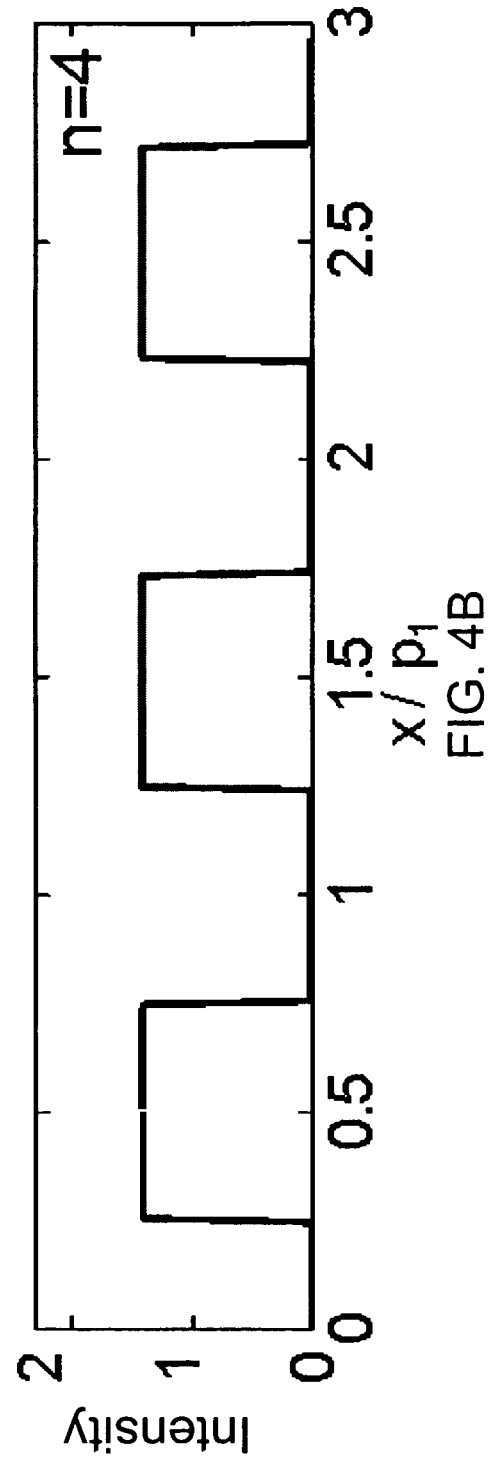
FIG. 4B is a schematic illustration of intensity profiles corresponding to transverse cross-sections for fractional Talbot order n=3 of the interference pattern of FIG. 2A.

Patent application US20050190882 to McGuire, entitled "Multi-spectral x-ray image processing" discloses a method of performing x-ray analysis on a body of unknown composition. The method comprises bombarding the body with a plurality x-ray beams, each x-ray beam having unique line spectra; and determining the compositional makeup of the body by detecting and analyzing x-rays reflected off of the body. Referring now to FIG. 1A, the above-referenced publications concerning interferometry-based imaging techniques are implemented by an interferometer device 100 that includes, inter alia, three different gratings and more specifically, a source grating 121, a beam splitter grating 122 and an absorption grating 123. Beam splitter grating 122 may have a grating as is schematically illustrated in FIG. 1B, wherein the height H of the structure may be such that the relative phase shift of X-rays passing through beam splitter grating 122 causes a phase shift on the X-rays of $\Delta\phi=\pi$ or an odd multiple thereof. Beam splitter grating 122 may thus also be referred to as phase grating 122. Moreover, if beam splitter grating's 122 duty cycle, which is defined as B/p equals 0.5, i.e., the width of the grating bars are equal to the width of the spaces, is illuminated by an X-ray plane wave (of wavelength $\lambda$) the incoming X-ray wave field is essentially divided into the two first diffraction orders. Since these two diffracted beams overlap almost completely an interference pattern is formed that changes depending on the distance d downstream of beam splitter grating 122. At some specific distances $d_n=(n/16)*D_{Talbot}$ (n=1, 3, . . . ), known as the fractional Talbot distances, a periodic pattern of linear fringes is observed. These fringes enable interpreting phase, as is for example outlined in patent application EP1731099. $D_{Talbot}$ is defined as the distance away from the initial wave front profile along the optical axis at which any laterally periodic wave front profile is replicated. If the grating, which forms the initial wave front profile, has periodicity P and wavelength $\lambda$, the Talbot distance may be found at $D_{Talbot}=2p^2/\lambda$. The phase-shift of an x-ray with energy E passing through a layer of thickness H is determined by the material's refraction index. The phase shift $\Delta\phi$ can thus be considered to be proportional to the material's thickness and the incident wavelength. Therefore, to achieve the required relative phase-shift of $\Delta\phi=\pi$ the depth of an appropriate grating increases with increasing x-ray energy. For example, in order to achieve a phase shift of $\Delta\phi=\pi$ in Si for X-ray at energy of 28 keV, the structure depth required in Si material has to be about H=35 μm and increases linearly with higher incident X-ray energy, as is schematically illustrated in FIG. 2. It should be noted that adjective and adverb "linear" and "linearly" also encompass the meaning "substantially linear" and "substantially linearly".

Towards higher X-ray energies not only deeper structure depths, but also smaller grating periodicity and thus higher aspect ratios (aspect ratio: structure depth H divided by the periodicity p) are required. Since the Talbot distance $D_{Talbot}$ and thus the dimension of the whole set-up scales according to the equation for the Talbot distance with $p_1^2$, the periodicity determines the compactness of the entire set-up and the dimensions of the gratings. Generally, an increase in the periodicity and/or structure depth of gratings renders the fabrication process of the gratings more difficult.

Referring now to conventional radiography a thick sample of a poorly absorbing material can come out in the same grey level in the radiograph as a thin but strongly absorbing one (known as the "overlapping problem" in radiography). In other words, the products of absorption coefficient ($\mu_a$) and travelling path length ($\mu_a*\Delta x$) through the sample are equal for both cases. In order to achieve elemental identification of the material under investigation many applications in conventional x-ray radiography thus use a set-up in which individual images are detected for two different energy ranges, i.e., dual energy radiography. Since the absorption coefficient $\mu_a$ scales with the electron density, the ratio of a first low energy (LE) and a second high energy (HE) measured intensity downstream an imaged object correlates with the energy of the imaging X-ray radiation incident on the object. Therefore, the absorption coefficient of the object being imaged and thus the object's material can be determined. The knowledge of electron density can then serve as an evidence for the material's (elemental) composition. As an example x-raying systems at airports use this technique in order to reliably detect potentially harmful metals and other illicit materials in the luggage.

Another method of X-ray imaging is known as Dual Energy X-ray Absorptiometry (DEXA) that is applied, for example, to determine bone density in people to detect thinning bones or osteoporosis.

Other methods than DEXA include tomography scans, which may yield similar results. However, compared to dual X-ray imaging, tomography scans may be time consuming, and the expended dose may be higher.

In general, dual X-ray imaging methods may implemented by so-called pseudo dual energy systems that may employ a single anode, a first and a second detector, wherein the two detectors are positioned in alignment to each other. The system further includes an absorber positioned between and in alignment with the two detectors. The first detector is implemented by a thin scintillator creating the image of the low energy part of the spectrum. The absorber (typically made of Cu or Al) absorbs the low energy tail of the incident X-ray. Therefore, the X-ray emanating from the absorber and incident on the second detector is the HE part of the X-ray. Accordingly, the image obtained from the second detector represents the image HE part of the X-ray. Instead of using the above-outlined setup to enable the pseudo dual-energy X-ray imaging method, dispersive digital image detectors may be employed, wherein detection thresholds for the X-ray energy is selectable.

DESCRIPTION OF THE INVENTION

Summary of Embodiments of the Invention

Embodiments of the invention disclose an interferometer device comprising an electromagnetic radiation source emitting radiation; a phase grating having a first aspect ratio; an absorption grating having a second aspect ratio; and a detector. The electromagnetic radiation source, the phase grating, the absorption grating and the detector are radiatively coupled with each other. The absorption grating is positioned between the detector and the phase grating; the electromagnetic radiation source is positioned in front of the source grating; and the phase grating is designed such to cause on at least one wavelength of radiation passing through the grating bars a phase shift ($\Delta\phi$) of less than $\pi$ relative to radiation passing between the grating bars with respect to the at least one wavelength.

In embodiments, the phase grating is designed such to cause one of the following phase shifts: $\pi/2$, $\pi/4$. In embodiments, the electromagnetic radiation source emits X-ray radiation having a mean energy of at least 20 keV, at least 40 keV, 60 keV, or at least 80 keV.

In embodiments, the electromagnetic radiation source may emit radiation in the visible, near or far infrared spectrum.

In embodiments the distance between said phase grating and absorption grating is chosen to be a fractional Talbot distance $d_{n1}$, and represented by the equation $d_{n1}=(n_1/8)*p_{522}^2/\lambda_{LE}$, wherein $n_1$ is a first integer and wherein $\lambda_{LE}$ is a first mean wavelength of said radiation having first mean energy $E_{LE}$.

In embodiments, the first integer $n_1$ is an even number.

In embodiments, the first aspect ratio of the phase grating is, for example, maximal one of the following: 8, 10 and 12.

In embodiments, a source grating is positioned between the electromagnetic radiation source and the phase grating, wherein the source grating is adapted to cause spatial coherence on the emitted radiation.

In embodiments, the electromagnetic radiation source is adapted to emit radiation at a second mean energy $E_{HE}$ for $\lambda_{HE}$, wherein the mean energy of $E_{HE}$ is a multiplication of $1/q$ with the mean energy $E_{LE}$, and wherein q takes values that range from 0 to 1.

In embodiments, the distance between said phase grating and absorption grating is chosen to be a fractional Talbot distance $d_{n2}$, represented by the equation $d_{n2}=(n_2/8)*p_{522}^2/\lambda_{HE}$, wherein $n_2$ is a second integer, and wherein $\lambda_{HE}/\lambda_{LE}=n_1/n_2$.

In embodiments, the second integer $n_2$ is an even number.

The present invention also discloses a method for performing interferometry comprising emitting electromagnetic radiation from an electromagnetic radiation source towards a phase grating having a first aspect ratio; effecting on at least one wavelength of radiation passing through the grating bars a phase shift ($\Delta\phi$) of less than $\pi$ relative to radiation of the at least one wavelength passing between the grating bars of the phase grating; absorbing at least some of the phase-shifted radiation emanating from said phase grating by an absorber grating; and detecting radiation emanating from the absorber grating.

In embodiments, the electromagnetic radiation is alternatingly or simultaneously emitted at a first mean energy $E_{LE}$ for $\lambda_{LE}$ and at a second mean energy $E_{HE}$ for $\lambda_{HE}$, wherein the mean energy of $E_{HE}$ is a multiplication of $1/q$ with the mean energy $E_{LE}$, and wherein q takes values that range from 0 to 1, thereby employing a dual-energy scheme.

DESCRIPTION OF THE INVENTION

It is an object of the invention to provide an alternative interferometry method and system. Embodiments of the present invention enable the imaging of objects at higher X-ray energies of, for example, at least 20 keV, at least 40 keV, or at least 80 keV at dual energy regimes by using an incoherent X-ray imaging source, wherein the imaging may be accomplished by employing interferometry. In other words, embodiments of the present invention may have a high degree of flexibility in performing interferometry with the X-ray energy, thereby allowing the implementation of a dual-energy set-up for elemental and/or material identification with X-ray having energy higher than, for example, 40 keV.

It should be noted that the term "coherent" and "monochromatic" as used herein as well as grammatical variations thereof also encompasses the meaning of the term "substantially coherent" and "substantially monochromatic", respectively.

It should further be noted that values of parameters indicated herein may also encompass its approximate values. Therefore, a phrase such as "phase shift $\Delta\phi=\pi$" may also include the meaning of "phase shift of approximately $\Delta\phi=\pi$".

In many fields of potential applications such as in industry or medicine higher X-ray energies are demanded in order to provide sufficient sample transmission. Therefore, by enabling interferometry with, e.g., X-rays at energies higher than, for example, 40 keV, the type of materials and objects that may be imaged is largely increased.

Embodiments of the invention comprise a beam splitter grating having an aspect ratio of for example, maximal 4, 6, 10 or 12 for respective energies, as well as a polychromatic and incoherent X-ray tube source. More specifically, the aspect ratio is such that $\Delta\phi<\pi$ (e.g. $\pi/2$, $\frac{1}{4}\pi$), thereby causing a corresponding reduction in the required structure depth H of the grating. Since the phase-shift obeys $\Delta\phi$ is proportional to $\lambda*H$, for instance the H=35 µm grating designed as a $\Delta\phi=\pi$ grating for 28 keV can also be used as a $\Delta\phi=\pi/2$ grating at X-ray energy 56 keV, or even as a $\pi/4$ grating at 112 keV.

It should be noted that the adjective "equal" as used herein also encompasses the adjective "substantially equal".

Reference is now made to FIG. 2A and FIG. 2B, wherein interference fringes are schematically illustrated in accordance to a simulation implemented by wave field propagation algorithms, wherein the phase shift is smaller than $\pi$ ($\Delta\phi<\pi$). These interference fringes are simulated for pure (non-absorbing) phase gratings designed to cause a maximal phase shift of, for example, $\Delta\phi=\pi$, when illuminated with a monochromatic and sufficiently coherent x-ray beam, as is for example disclosed in Patent application EP1623671.

In FIG. 2A, parameters of a first grating (not shown) are chosen to simulate for a plane wave (with wavelength $\lambda$) incident thereon a phase shift of $\Delta\phi=\pi/2$, wherein in FIG. 2B, parameters of a second grating (not shown) are chosen to simulate for a plane wave having wavelength $\lambda$ incident on the second grating, a phase shift of $\Delta\phi=\pi/4$.

As can readily be seen, the interference fringes resulting from the phase shift $\Delta\phi=\pi/2$ (FIG. 2A) are more pronounced compared to the fringes that result from phase shift $\Delta\phi=\pi/4$ (FIG. 2B). For the phase shift of $\Delta\phi=\pi$, the distances of the appearing fringes were found at fractional Talbot distances with odd n (i.e., n=1, 3, 5 or 7). In contrast, for phase shifts $\Delta\phi\leq\pi/2$ the best pronounced fringes appear at even fractional Talbot distances of n=2, 4 and 6.

Making additional reference to FIG. 3A, FIG. 3B, FIG. 4A and FIG. 4B, intensity profiles of interference fringes at Talbot distances n=1, 2, 3, 4, respectively, for $\Delta\phi=\pi/2$ along the simulated propagation of the wavefront are schematically illustrated.

Please note that the duty cycle of the grating causing, for example, a phase shift of $\Delta\phi=\pi/2$ or $\Delta\phi=\pi/4$, may be the same for the grating causing a phase shift of $\Delta\phi=\pi$. However, a decrease in phase shift by for example a factor of 2 from $\pi$ to $\pi/2$, causes a corresponding reduction in the periodicity of the interference fringes. A reduction in the periodicity of the interference fringes may enable a corresponding reduction in the periodicity of an absorption grating of an interferometer according to an embodiment of the invention, as outlined hereinafter.

Figure 5:
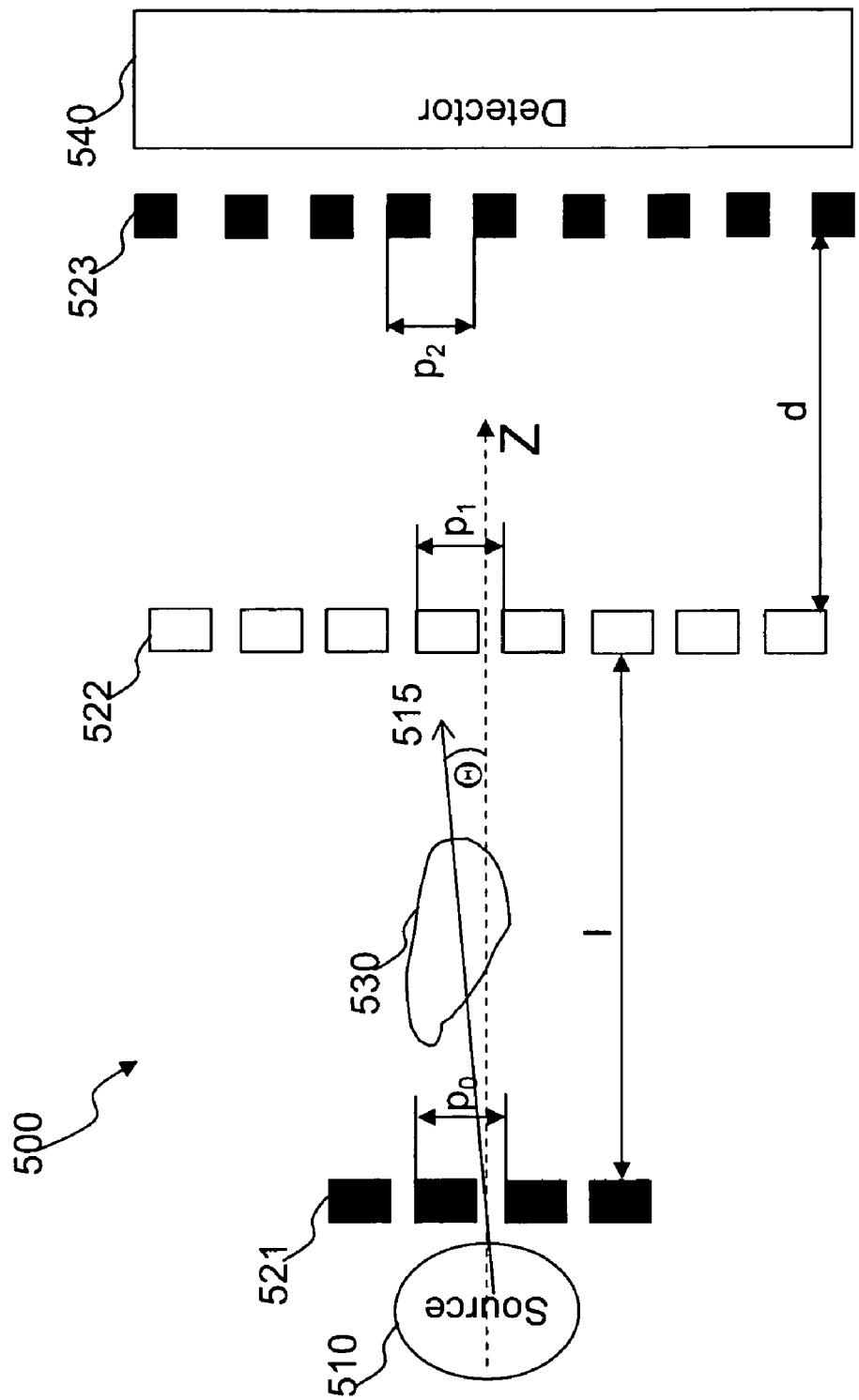
FIG. 5 is a schematic illustration of setup of an X-ray imaging device, according to an embodiment of the invention.
Figure 6A:
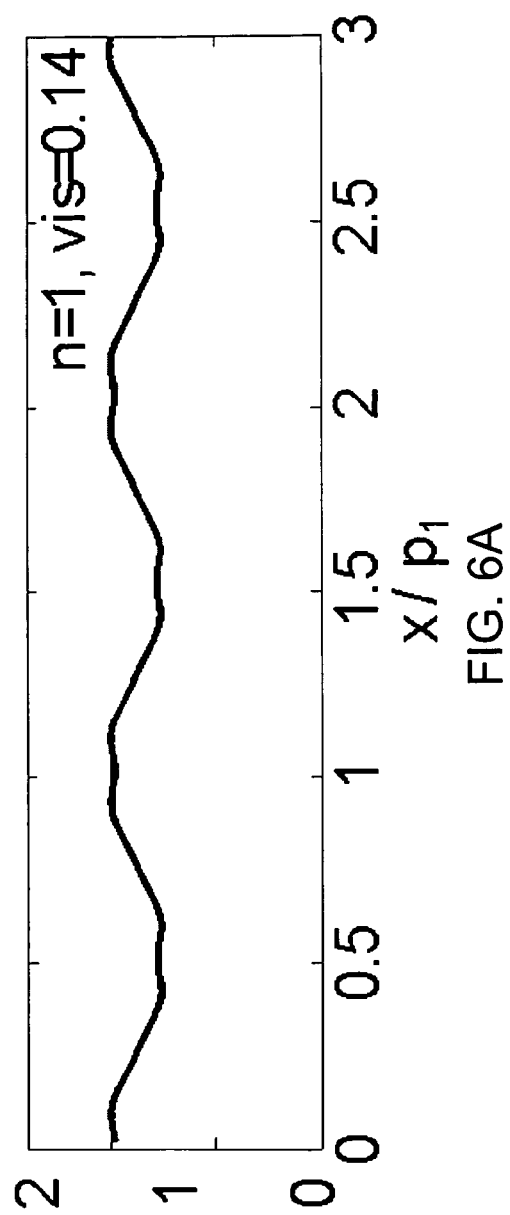
FIG. 6A schematically illustrates interference fringes at fractional Talbot distances n=1 obtained from simulation of $\Delta\phi = \pi/2$-interferometer optimized for E=28 keV and Ag anode source at 35 keV, according to an embodiment of the invention.
Figure 6B:
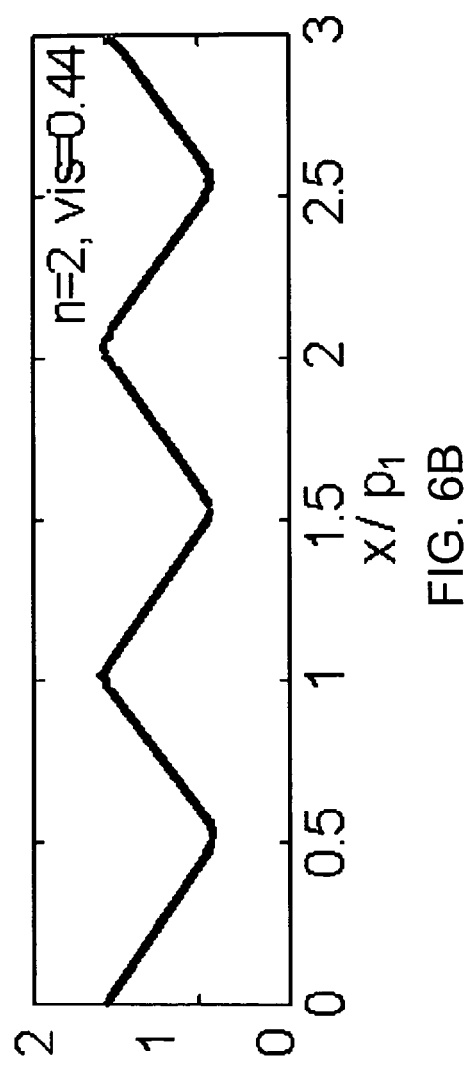
FIG. 6B schematically illustrates interference fringes at fractional Talbot distances n=2 obtained from simulation of $\Delta\phi = \pi/2$-interferometer optimized for E=28 keV and Ag anode source at 35 keV, according to an embodiment of the invention.
Figure 7A:
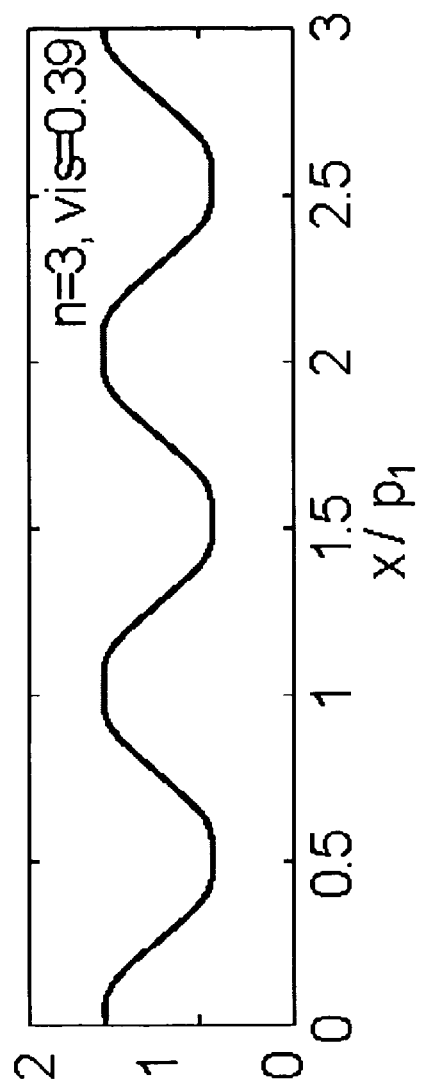
FIG. 7A is a schematic illustration of intensity profiles of interference fringes at fractional Talbot distances n=3 obtained from simulation of $\Delta\phi = \pi/2$-interferometer optimized for E=28 keV and Ag anode source at 35 keV, according to an embodiment of the invention.
Figure 7B:
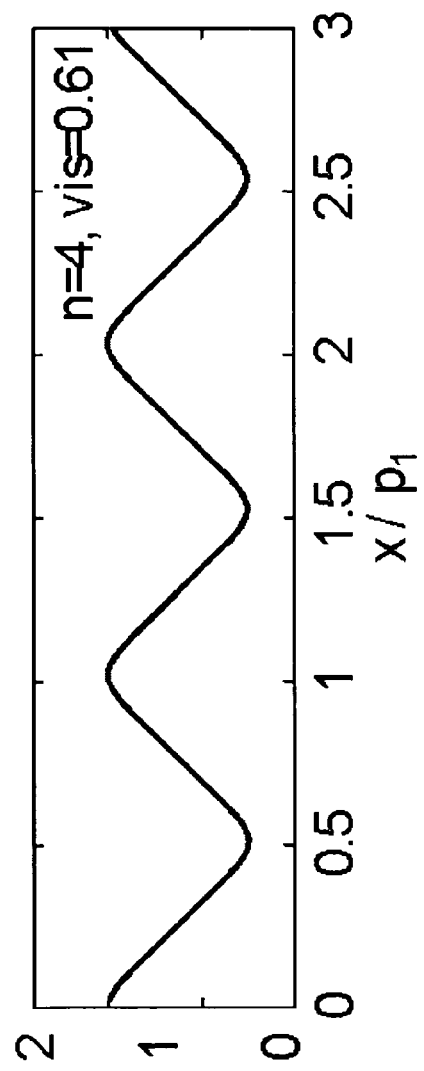
FIG. 7B is a schematic illustration of intensity profiles of interference fringes at fractional Talbot distances n=4 obtained from simulation of $\Delta\phi = \pi/2$-interferometer optimized for E=28 keV and Ag anode source at 35 keV, according to an embodiment of the invention.

Further reference is now made to FIG. 5. According to an embodiment of the invention, an interferometer device 500 may include a radiation source 510, a source grating 521, a beam splitter grating or phase grating 522, an absorption grating 523, and a detector 540, all of which are coupled with each other with reference to electromagnetic radiation.

It should be noted that a first element or arrangement is considered to be coupled to a second element or arrangement with reference to the electromagnetic radiation, if at least some electromagnetic radiation emanating from the first element or arrangement is incident on the second element or arrangement.

Radiation source 510 be adapted to emit polychromatic and/or incoherent X-ray radiation 515, source grating 521 is designed to absorb at least some of the radiation incident thereon, and phase grating 522 may be designed such to cause a phase shift of $\Delta\phi<\pi$ on the non-absorbed radiation incident thereon, between radiation passing through the grating bars of phase grating 522 and the radiation passing in-between the grating bars of phase grating 522.

In comparison to the ideal mono energetic case, for which the interference fringes are schematically illustrated in FIG. 3, the pattern of the interference fringes for incoherent and polychromatic radiation will become rather smeared, because the whole x-ray source energy spectrum of radiation 515 may contribute to that pattern. However, to enable analyzing the interference fringes anyway, a measure for the phase sensitivity is introduced herein, namely, fringe visibility, which is herein defined as the relative amplitude height of the fringe profile recorded in transverse direction at a given distance away from the beam splitter grating and thus for example by the following equation:

$$\text{Visibility} = \frac{I_{max} - I_{min}}{I_{max} + I_{min}} \quad (1)$$

wherein, $I_{max}$ and $I_{min}$ are the maximum and the minimum intensity of a fringe profile, respectively, measured from a given distance from phase grating 522. Parameters, which enable the simulation of interaction of X-ray 515 with matter, may be based on empirical data. Furthermore, parameters may be introduced that represent grating imperfections such as local variations of structure depth, periodicity or duty cycle of phase grating 515.

Referring now to FIG. 6A, FIG. 6B, FIG. 7A and FIG. 7B, the simulated interference fringe profiles are respectively shown at fractional Talbot distances n=1, 2, 3 and 4 for the following conditions:

Radiation source 510: X-ray tube employing an Ag-anode operated at 35 kV and E=28 keV;
Source grating 521: DC=0.1;
phase grating 522: phase shift $\Delta\phi=\pi/2$, H=17.5 μm, DC=0.5;
absorption grating 523: DC=0.5

Figure 8:
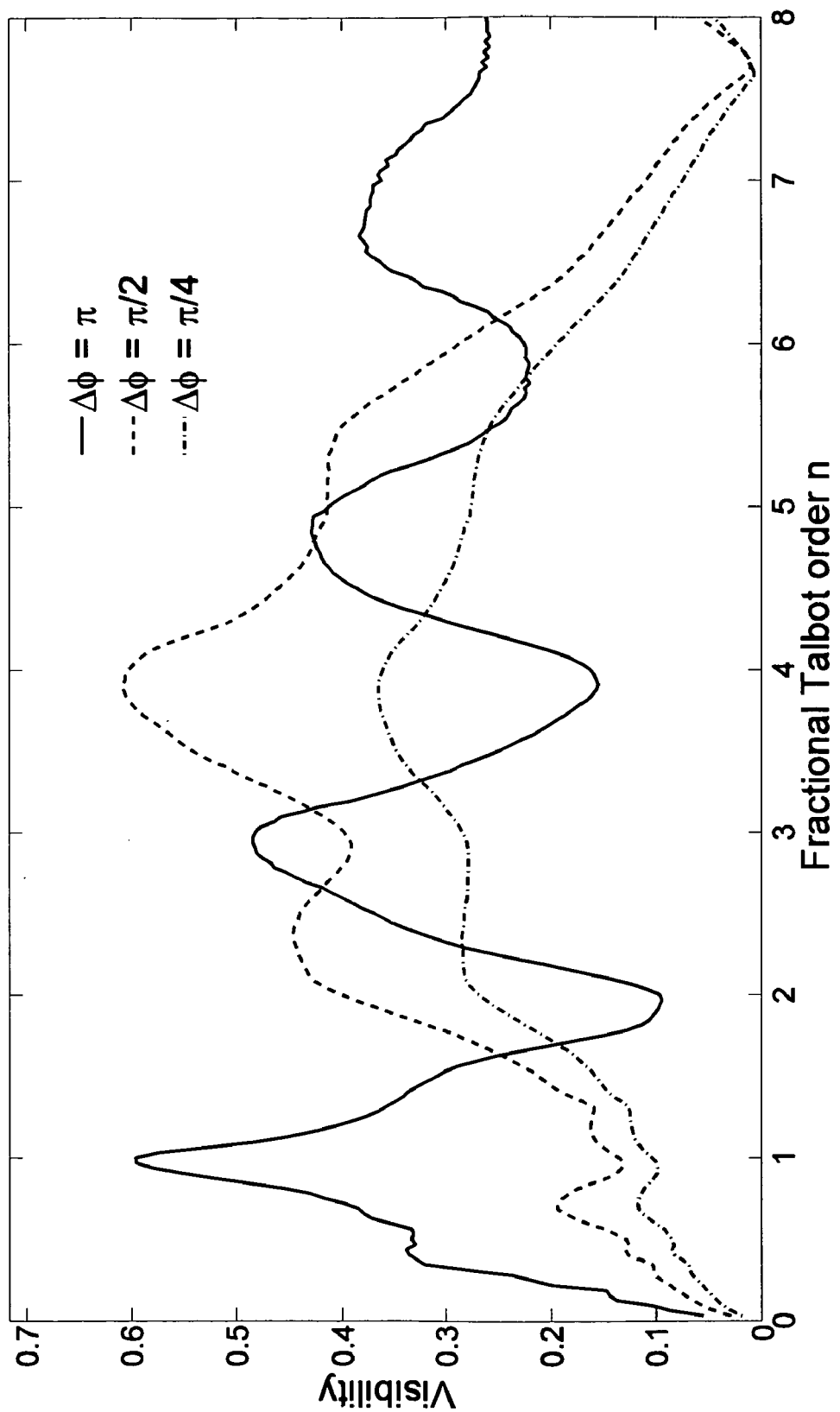
FIG. 8 is a schematic illustration of a graph of fringe visibility as a function of the fractional Talbot order n for a beam splitter grating with for $\Delta\phi = \pi$, $\Delta\phi = \pi/2$ and $\Delta\phi = \pi/4$ for a polychromatic energy spectrum with a peak of $\Delta E/E \approx 30\%$ around the energy for which the interferometer of FIG. 5 is designed.

Referring now to FIG. 8, the visibility is shown as a function of the distance away from phase grating 522 for the three cases (i) $\Delta\phi=\pi$ (H=35 μm), (ii) $\Delta\phi=\pi/2$ (H=17.5 μm) and (iii) $\Delta\phi=\pi/4$ (H=8.75 μm).

Fringe visibility for the polychromatic and incoherent radiation 515 for phase shift of $\Delta\phi=\pi$ is maximal at odd Talbot orders (1, 3, 5, 7, . . . ), and for phase shifts of $\Delta\phi=\pi/2$, and $\pi/4$, the visibility is maximal at even Talbot orders (2, 4, 6, . . . ). The maxima of the fringe visibility for polychromatic and incoherent radiation thus correspond to the maxima of fringe visibility for monochromatic and coherent radiation.

Similar results may also be obtained for any simulated X-ray energy other than 28 keV exemplified herein, if the energy spectrum of radiation 515 emitting from source 510 matches interferometer device 500 such that the shape of the spectrum of radiation 515 of is a broad peak around the energy E such that $\Delta E/E$ is for example maximal $\approx$30%, whereby $\Delta E$ stands for the width of the X-ray spectrum. Generally, fringe visibility increases with decreasing $\Delta E/E$, i.e., the narrower the peak, the better the visibility.

The fringe visibility of the interferometer improves the narrower the peak of the effective spectrum of radiation 515 incident on source grating 521. Such a peak may be obtained by employing suitable absorbing filters, whereby the filters may made of any suitable material which show absorption K-edges at specific energies that result in the appropriate shaping of the source spectrum.

The narrower the peak, the higher the visibility gets, but the more of the x-ray flux is wasted. Since the wave field propagation is a function of the product of the wavelength and propagation distance ($\lambda*d$) only, an interval in propagation direction is equivalent to an interval in wavelength or energy $\Delta E$. Since for $\Delta\phi=\pi/2$ and $\Delta\phi=\pi/4$ the visibility functions 810 and 820 are relatively smooth and resemble a broad ridge, an increase in $\Delta E$ does not substantially reduce the respective visibility. Accordingly, an increase in $\Delta E$ may in general not have much of an impact on the visibility for $\Delta\phi=\pi/2$ and Δφ=π/4. Therefore, interferometry may be performed without additional filtering (except for the source exit window, typically 1 mm Be or Al) for a wide range of spectra corresponding to ΔE/E≈30%, thereby possibly obtaining a reduced exposure time due to increased photon flux and count rates, which would otherwise be diminished when employing absorbing filters. Accordingly, radiation source 510 of interferometer device 500 may be filter-free.

Figure 9:
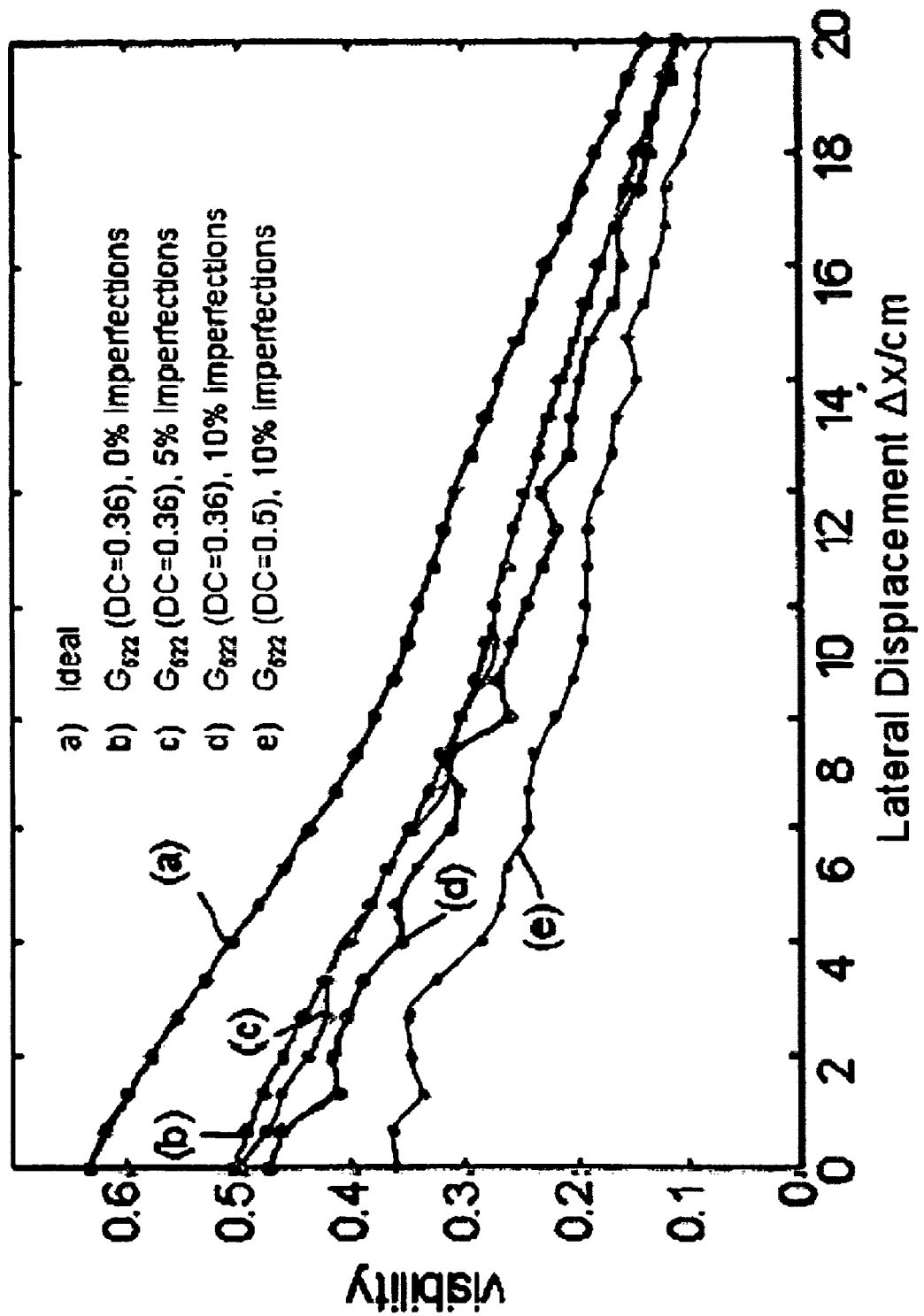
FIG. 9 is a schematic illustration of graphs of visibility in dependence on the field of view between phase gratings for $\Delta\phi = \pi$, according to an embodiment of the invention.
Figure 10:
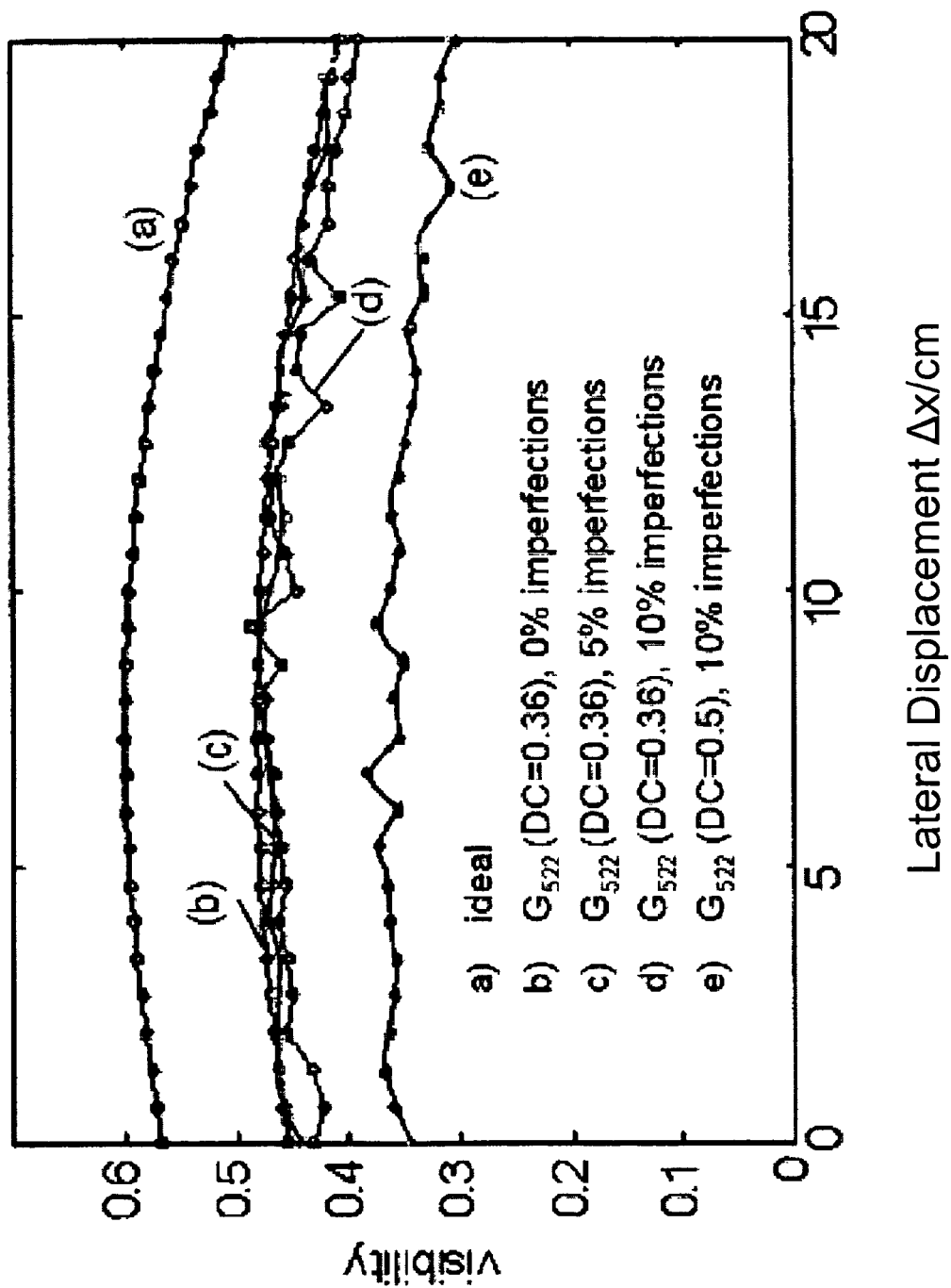
FIG. 10 is a schematic illustration of graphs of visibility in dependence on the field of view between phase gratings for $\Delta\phi = \pi/2$, according to an embodiment of the invention.

Reference is now made to FIG. 9 and FIG. 10, wherein the visibility respectively for Δφ=π and Δφ=π/2 for various duty cycles of the source grating 521 and percentages of imperfections are schematically illustrated. The horizontal coordinate Δx/cm corresponds to the transverse offset away from the optical axis in interferometer device 500, wherein the distance between source grating 521 and phase grating 522 is about 1.5 meters. As can readily be seen in FIG. 10, by employing an aspect ratio for phase grating 522 designed for energy of about 28 keV and phase shift of about Δφ=π/2) the visibility remains generally constant for non-orthogonal angles incidence, i.e., there is no substantial loss of visibility for non-orthogonal angles of incidence. Therefore, a large field-of-view (FOV) and/or a relatively short distance l may be feasible for interferometry. The angle of incidence may be, for example. θ=arctan((FOV/2)/l)=π/20.

It should be noted that several constraints have to be met in order to fulfil the condition of interference in interferometer device 500. These constraints may be expressed, for example, by the following equations:

$$D_n = n \cdot \frac{p_1^2}{8\lambda} \quad (2)$$

$$\frac{\eta \cdot p_2}{p_1} = \frac{l+d}{l} \quad (3)$$

and $$\frac{p_0}{p_2} = \frac{l}{d} \quad (4)$$

wherein equation (1) describes the Talbot distance, equation (2) the divergence of the emitted radiation 515, and equation (3) the constraints for source grating 521.

It follows from equation (3) and (4) that $$p_1 = \frac{\eta \cdot p_0 \cdot p_2}{p_0 + p_2} \quad (5)$$

wherein θ=1 for Δφ<π (and θ=2 for the state-of-the-art case Δφ=π). It should be noted that the parameter θ takes into account that due to the high degree of symmetry for phase grating 522 effecting a phase shift of Δφ=π, the periodicity of the (transverse) interference pattern generated at odd fractional Talbot distances is essentially half of grating periodicity of phase grating 522, and no interference fringes may be present at even fractional Talbot distances. However, if phase grating 522 is designed to effect a phase shift of Δφ<π, the periodicity of the interference fringes is equal to the grating periodicity of phase grating 522. Therefore, the aspect ratio of absorption grating 523 designed to absorb for a phase shift of Δφ<π may be roughly at least smaller than, for example, 35, 25, 10 or 5.

The distances d and l from the gratings may be expressed by the following equations (6) and (7) respectively:

$$d_n = D_n \frac{p_0 + p_2}{p_0} \quad (6)$$

$$l = d_n \cdot \frac{p_0}{p_2} \quad (7)$$

It follows from the equations above that by choosing the grating periodicity of two gratings (e.g., source grating 521 and absorption grating 523) the third periodicity (e.g., phase grating 522) of interferometer device 500 is determined. More specifically, the wavelength λ, the Talbot order n, remaining grating periodicity (e.g., phase grating 522, if periodicities for source grating 521 and absorption grating 523 are chosen), as well as the distance l between source grating 521 and phase grating 522, and distance d between phase grating 522 and absorption grating 523 are set accordingly. Hence, in order to enable performing interferometry with small wavelengths (e.g., X-ray radiation) two grating periodicities initially chosen have to be sufficiently small. The following are exemplified values for interferometer device 500:

$p_0$: 1 μm-200 μm
$p_1$, $p_2$: 0.2 μm-40 μm
l: 0.1 m-5 m
d: 0.1 cm-100 cm

In general the distances l and d are increasing with decreasing λ (increasing energy) and they are decreasing with decreasing periodicities. Going towards higher energies thus demands for shorter periodicities for the gratings in order to keep the set-up as compact as possible. On the other hand higher energy also demands for deeper gratings which also pushes the gratings to have aspect ratios as large as possible. However, by designing phase grating 522 such that Δφ<π (e.g., Δφ≦π/2) the aspect ratio of absorption grating 523 is only half than in the case with Δφ=π.

It should be noted that in general, the periodicity $p_{521}$ of source grating 521 may in general be larger than the periodicities of phase grating 522 and absorption grating 523. Consequently, by designing phase grating 522 such that, for example, Δφ=π/2, interferometry on radiation of, e.g., X-ray at energies higher than, e.g., 20 keV, 50 keV, 80 keV, may be performed whilst keeping the aspect ratios of source grating 521, phase grating 522 and absorption grating 523 below, e.g., 10, whereby distances l and d scale accordingly.

Based on equations 2-7, distances l and d of interferometer device 500 may be approximated as follows:

$$d \approx \frac{n\eta^2 p_2^2}{8\lambda} \equiv n\eta^2 D_0 \quad (8)$$

and $$l \approx \frac{n\eta^2 p_0 p_2}{8\lambda} = n\eta^2 L_0 \quad (9)$$

From there it follows that, for example, for Δφ=π/2, n=2 or 4→$p_1$≈$p_2$→d≈2*$D_0$ or 4*$D_0$, and l=2*$L_0$ or 4*$L_0$, respectively. Correspondingly, by causing a phase shift of for example π/2, interferometry for radiation having energies of at least, e.g., 40 keV, may be performed by interferometer device 500 without necessarily needing to increase the distances l and d. Therefore, despite a possible increase by a given factor of incident radiation energy on embodiments of interferometer device 500, the gratings may in the respective embodiments be designed to cause phase shifts such that the sum of the distances between the gratings may be changed by a second factor, which is smaller than the first factor. In some embodiments for example, an increase of the radiation energy by first factor of 2 may cause an increase in the sum of the distances d and l by second factor 1. Accordingly, the distances between the gratings may in some embodiments be retained despite the increase in radiation energy. In some embodiments, the ratio between the first factor (factor of increase in radiation energy) and the second factor (factor of increase of the sum of the distances d and l) may be maximal, for example, 2, 1.7, 1.6, or 1.5.

Design parameters for embodiments of interferometer device 500 are exemplified herein.

For $\Delta\phi=\pi/4$ and $\lambda=0.0443$ nm (28.0 keV):
$p_{521}=73.0$ μm, $p_{522}=1.95$ μm, $p_{523}=2.0$ μm; l=160.1 cm, d=4.4 cm, n=2, aspect ratio of phase grating 522: 4.5.

For $\Delta\phi=\pi/4$ and $\lambda=0.0443$ nm (28.0 keV):
$p_{521}=73.0$ μm, $p_{522}=1.95$ μm, $p_{523}=2.0$ μm; l=80.1 cm, d=2.2 cm, A=0.0443 nm (28.0 keV), n=2, aspect ratio of phase grating 522: 8.9

For $\Delta\phi=\pi/2$ and $\lambda=0.0222$ nm (56.0 keV):
$p_{521}=35.0$ μm, $p_{522}=3.94$ μm, $p_{523}=4.44$ μm; l=155.5 cm, d=19.7 cm, n=2, aspect ratio of phase grating 522: 8.9

Correspondingly, in some embodiments of the invention, distance l may not exceed, for example, 180 cm, 170 cm, 168 cm, 165 cm, 163 cm, 160.5 cm or 160.1 cm; and distance d may not exceed, for example, distances of 25 cm, 20 cm, 19.7 cm, 6 cm, or 4.4 cm.

Figure 11:
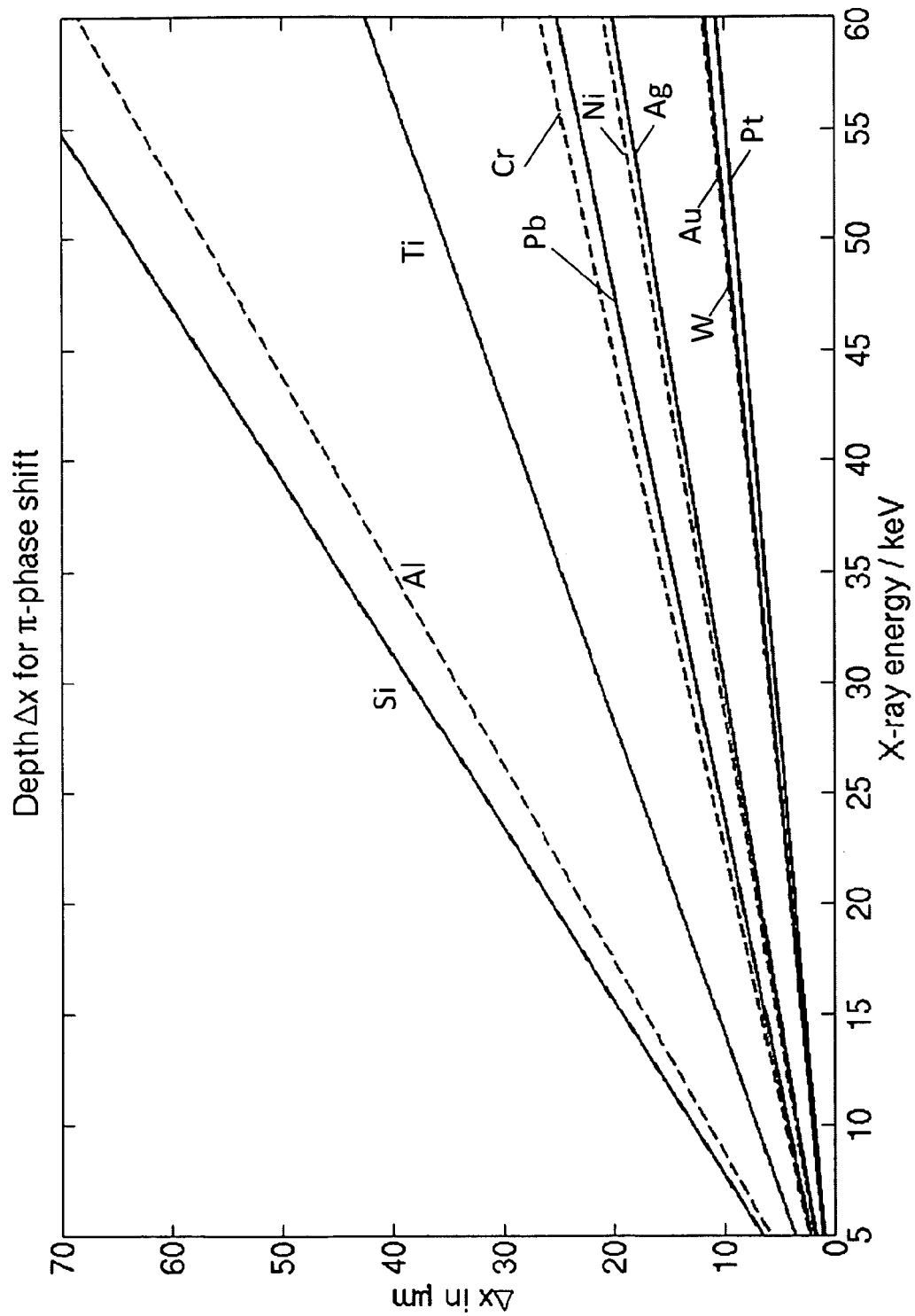
FIG. 11 is a schematic illustration of graphs for the depth of gratings vs. incident radiation energy to achieve a phase shift of $\Delta\phi = \pi$ in respective materials according to embodiments of the invention.

Reference is now made to FIG. 11. Gratings such as, for example, phase grating 522, may be made of various materials. Examples of such materials may include but are not limited to Si, Al, Ti, Pb, Cr, Ni, Ag, W, Au, Pt, and/or any other suitable materials and/or compound of materials, wherein the depth H required for obtaining a particular phase shift may vary for the different materials. For example, as is schematically illustrated in FIG. 11, the depth H required to obtain for radiation with energy of about 30 keV a phase shift of $\Delta\phi=\pi$ is about 4 times higher in material Si than in material Ni.

Reference is now made to FIG. 12A and FIG. 12B. According to some embodiments of the invention, interferometer device 500 may be employed in conjunction with a dual energy scheme, as outlined hereinafter. Implementing a dual energy phase contrast measurement can provide additional information on the elemental composition of object 530 because its refractive index $n=1-\delta(\lambda)$, which gives rise to the phase shift $\Delta\phi$, which is proportional to $\delta*\Delta x$ (where $\Delta x$ is the medium's thickness), scales with the radiation energy incident to object 530 and with the electron density of the material of object 530. Thus, from the ratio of intensity measured with the image radiation detector 540 of the phase images acquired at two different X-ray energies, the ambiguity between penetration depth and refraction index for object 530 becomes resolvable.

Dual-energy Scheme:

By employing interferometer device 500, wherein phase grating 522 causes a phase-shift of, for example, $\Delta\phi<\pi$ (e.g., $\Delta\phi<\pi/2$, $\Delta\phi<\pi/4$), separate phase sensitive measurements in two or more complementary energy domains may be performed, as outlined hereinafter.

Considering, for example, a first and a second plane wave LE and HE having energies $E_{LE}$ and $E_{HE}$ respectively, wherein, e.g., $E_{HE}=2*E_{LE}$, the corresponding wavelengths are $2*\lambda_{HE}=\lambda_{LE}$.

Interferometry according to a dual-energy scheme with waves LE and HE may be performed, if the set-up parameters of interferometer device 500 (i.e., the grating periodicities $p_{521}$, $p_{522}$, $p_{523}$, as well as distances l between source grating 521 and phase grating 522, and distance d between phase grating 522 and absorption grating 523) meet all the constraints that enable obtaining interference for wave LE as well as for wave HE. In some embodiments, the depth H of phase grating 522 designed such to shift the phase of the first plane wave by $\Delta\phi_1<\pi$, may shift the phase of the second plane wave by, for example, half of the of the phase shift of the first plane wave ($\Delta\phi_2=\Delta\phi_1/2$). For example, if phase grating 522 is designed to cause on the first plane wave $E_{LE}$ a phase shift of, e.g., approximately $3/4*\pi$, $\pi/2$, or $\pi/4$, the phase shift caused on the second plane $E_{HE}$ wave may approximately be, $3/8*\pi$, $\pi/4$, or $\pi/8$, respectively.

The amplitude interference patterns for $\lambda_{LE}$ and $\lambda_{HE}$ are schematically illustrated in FIG. 12A and FIG. 12B, respectively. In FIG. 12A, the total distance along optical axis Z corresponds to the Talbot distance of the $E_{LE}$ wave: $D_{Talbot}(\lambda_{LE})=2*p_{522}^2/\lambda_{LE}$, and in FIG. 12B, the total distance along the optical axis Z corresponds to the Talbot distance of the $E_{HE}$ wave: $D_{Talbot}(\lambda_{HE})=2*D_{Talbot}(\lambda_{LE})$. Therefore, in FIG. 12B only half of the Talbot distance is shown for $E_{HE}$. As can readily be seen from FIG. 12A and FIG. 12B, the interference pattern for the plane wave with $E_{HE}$ is very similar to the one with $E_{LE}$, but stretched by a factor two along optical axis Z. Therefore, as is schematically indicated by dashed line 1210, the distance of fractional Talbot order n=4 of plane wave LE coincides with the fractional Talbot order n=2 of plane wave HE. Thus, the maximum of contrast for both the LE and HE wave may occur at a distance $d=1/4*D_{Talbot}(\lambda_{LE})=1/8*D_{Talbot}(\lambda_{HE})$.

In principle the relation between the radiation energies $E_{LE}$ and $E_{HE}$ can be $E_{LE}=q*E_{HE}$ with any $q\in(0, 1)$, i.e., the mean energy of $E_{HE}$ is a multiplication of 1/q with the mean energy $E_{LE}$, and wherein q takes values that range from 0 to 1

It follows from there:

$$\frac{n_{HE}}{n_{LE}} = q \quad (10)$$

Equation 10 is a condition required for the adoption of the dual energy scheme explained herein. If in addition to said condition, phase grating 522 causes a relative phase shift of, $\Delta\phi<\pi$ (e.g., $\Delta\phi=\pi/2$ or $\Delta\phi=\pi/4$), then the periodicity of the interference patterns for waves HE and LE are equal at any distance away from the grating, in particular at the distance that corresponds to the Talbot orders $n_{LE}$ and $n_{HE}$ for the LE and the HE wave, respectively. More specifically, "stretching" is only in longitudinal direction along the optical axis/direction of propagation. There is now stretching in transverse direction. The periodicity of the interference fringes is in transverse direction and since no stretching in this direction occurs, they are (substantially) equal to the periodicity of the phase grating 522.

Therefore, in principle any q is allowed. In some embodiments however, values for $q=n_{HE}/n_{LE}$ are chosen such to be compatible with these fractional Talbot orders (e.g., $n_{LE}=4$, $n_{HE}=2$), thereby possibly optimizing the fringe visibility for both wave LE and HE. The two recorded images of interference represent the yield of x-rays from disjunctive energy intervals. In other words: the visibility fringes have to be individually formed for a broad peak around the design energies $E_{LE}$ and $E_{HE}$ each. In general, to achieve this task, source 510 may in some embodiments of the invention provide locally and/or temporally separated disjunctive energy spectra, and/or detector 540 may be adapted to discriminate the energy of the detected X-rays.

Embodiments of source 540 may include, for example, usage of two different x-ray tubes providing individual sources for HE and LE measurement (dual source system). It is possible to perform one measurement after the other and/or to perform the measurements locally separated. In principle it is not necessary that source 510 embodies two separate sources. Instead, a single anode may be employed operable at alternating voltage biases.

In embodiments, appropriate filters in front of source 510 may be employed that cut-off either the low energy or the high energy part of the spectrum of the emitted radiation.

In embodiments, source 510 may comprise, e.g., of two (or more) different anodes, whereby the different anode materials may be operable with different acceleration voltage or even in a pulsed way (by means of a variable high voltage supply) providing thus a pattern of temporally switching between HE and LE source. Additionally, source 510 may employ several acceleration stages wherein the electron beam(s) may be mutually deflected to either one of the anodes. Optionally, filters may be introduced into the extracted x-ray beam to shape the energy spectrum incident on object 530.

Additionally or alternatively, source grating 521 may be integrated with the tube source 510. Optionally, source 510 may employ a structured anode, which, when irradiated by the electron beam, may form an array of individual spatial coherent but mutually incoherent line sources. In some embodiments, source 510 may comprise an aperture adapted to create a grating-like structure of the electron beam hitting the anode or that a sufficiently well collimated and/or focused electron beam is scanned over the anode. Such embodiments may of particular interest in terms of a so-called "phase stepping" measurement procedure. It may for example be required that either one of the three gratings is scanned in transverse direction perpendicularly to the grating bars. By scanning the source electron beam or using an aperture, the pattern at which the electrons hit the anode can be altered. More specifically, one phase contrast image requires a series of individual exposures for which the relative position of one grating (e.g., the source grating 521) is sequentially shifted in the transverse direction (orthogonal to the optical axis and orthogonal to the grating bars). Alternatively, the position of the electron beam hitting the anode (and thus the generation of the scanning X-ray beam) can be steered to achieve sequential shifting.

Referring now to detector 540, pseudo-dual energy systems comprising of a first and a second detector, the first being positioned in front of the second, with an absorber in between the first and the second detector, may be employed. More specifically, a first (front) detector may be embodied by a thin scintillator adapted to create the image of the low energy part of the spectrum incident on the scintillator. An absorber radiatively coupled behind the scintillator may cut off the low energy tail in the spectrum and thus the image obtained from the second detector may represent an image of the HE wave.

In some embodiments, detector 540 may be embodied by a detector enabling energy dispersive single photon counting. Thus, individual images can be built that count only events registered either as belonging the low energy or the high energy domain. A dual energy scheme can thus be implemented by applying appropriate energy thresholds on detector 540.

It should be noted that the ways according to which source 510 and detector 540 may largely depend on the requirements of a specific application. It should further be noted that the above-outlined embodiments may be combined in many ways and should not be considered to be merely implementable in separate embodiments of the invention. For example in medical applications, radiation dose may be the most important factor to optimize for both source 510 and detector 540. Counting efficiency for detector 540 may have to be as high as possible, whilst source 510 may be optimized such to merely give rise to image contrast.

Embodiments of the present invention are compatible with existing absorption radiography.

It should be noted that embodiments of the present invention enable providing both information regarding phase as well as an absorption of radiation 515 by object 530. More specifically, embodiments of the present invention enable resolving ambiguities ("overlapping problem") as well in the absorption- as in the phase-contrast imaging mechanism. Since the two contrast mechanisms are based on measurements of different physical quantities (i.e., phase and absorption) the ambiguities any particular application might suffer from may not be the same. For example, a single exposure delivers both the phase contrast image and the absorption radiograph of object 530. Therefore, information on materials identification can be volumetrically rendered for both the absorption- and the phase-contrast mechanism. This means that correlation between the information on materials identification based on either absorption coefficient or refraction index can be achieved in a three dimensional way.

The following, parameters of a dual energy setup designed for energies are presented as an example.

| | LE | HE |
|---|---|---|
| n: | 4 | 2 |
| $\Delta\Phi$: | $\pi/2$ | $\pi/4$ |
| E: | 40.0 keV | 80.0 keV |
| $\lambda$: | 0.0310 nm | 0.0155 nm |
| $(p_{521}, p_{522}, p_{523})$: | (35.0 µm, 3.18 µm, 3.5 µm) | |
| (l, d): | (179.4 cm, 17.9 cm) | |
| Aspect ratio (phase grating 522): | 7.9 | |

Embodiments of the present invention may be used for medical imaging, medical diagnostics, quality inspection, security screening, non-destructive testing, material sciences, and the like. Embodiments of the present invention may for example be employed in conjunction with tomography, wherein object 530 is rotated around its axis and exposures are taken at discrete rotation angles. Alternatively, interferometer device 500 may be rotated around object 530.

In general the absorption coefficient of any material drops quite rapidly with increasing energy (unless so-called K-edges are present in the energy interval under consideration), which is of particular importance in absorption radiography, since image contrast is achieved by the radiation absorbed by the sample. However, since the refraction index drops less rapidly with increasing energy and moreover it is in general higher than the absorption coefficient of any particular material, phase contrast can be achieved at higher x-ray energy with reduced radiation dose. For instance in applications that investigate soft tissue, e.g. in mammography, higher energies can be applied in phase contrast imaging than in standard radiography systems without suffering from poorer image contrast but with the benefit of substantially reduced radiation dose absorbed by the specimen.

It should be understood that an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions.

It should be understood that the phraseology and terminology employed herein is not to be construed as limiting and is for descriptive purpose only.

The principles and uses of the teachings of the present invention may be better understood with reference to the accompanying description, figures and examples.

It should be understood that the details set forth herein do not construe a limitation to an application of the invention. Furthermore, it should be understood that the invention can be carried out or practiced in various ways and that the invention can be implemented in embodiments other than the ones outlined in the description below.

It should be understood that the terms "including", "comprising", "consisting" and grammatical variants thereof do not preclude the addition of one or more components, features, steps, integers or groups thereof.

The meaning of "in" includes "in" and "on". The term "based on" is not exclusive and provides for being based on additional factors not described, unless otherwise indicated.

If the specification or claims refer to "an additional" element, that does not preclude there being more than one of the additional element.

It should be understood that where the claims or specification refer to "a" or "an" element, such reference is not to be construed as there being only one of that element.

It should be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The term "method" and "process" refers to manners, means, techniques and procedures for accomplishing a given task including, but is not limited to those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein ought to be commonly understood as by one of ordinary skill in the art to which the invention belongs, unless otherwise defined.

The present invention can be implemented in the testing or practice with methods and materials equivalent or similar to those described herein.

While the invention has been described with respect to a limited number of embodiments, these should not be construed as limitations on the scope of the invention, but rather as exemplifications of some of the embodiments. Those skilled in the art will envision other possible variations, modifications, and programs that are also within the scope of the invention. Accordingly, the scope of the invention should not be limited by what has thus far been described.

What is claimed is:

1. An interferometer device, said device comprising:
an electromagnetic radiation source emitting radiation;
a phase grating having a first aspect ratio and comprising grating bars;
an absorption grating having a second aspect ratio; and
a detector;
wherein said electromagnetic radiation source, said phase grating, said absorption grating and said detector are radiatively coupled with each other;
wherein said absorption grating is positioned between said detector and said phase grating;
wherein said electromagnetic radiation source is positioned in front of said source grating; and
wherein said phase grating is designed such to cause on at least one wavelength of radiation passing through the grating bars a phase shift $\Delta\phi$ of less than $\pi$ relative to radiation passing between the grating bars respective to said at least one wavelength.

2. The interferometer device of claim 1, wherein said phase grating is designed such to cause one of the following phase shifts ($\Delta\phi$): $\pi/2$, $\pi/4$.

3. The interferometer device of claim 1, wherein said electromagnetic radiation source emits X-ray radiation having a mean energy of at least either one of the following: 20 keV, 40 keV, 60 keV, and 80 keV.

4. The interferometer device of claim 1, wherein the distance between said phase grating and absorption grating is chosen to be a fractional Talbot distance $d_{n1}$, and represented by the equation $d_{n1}=(n_1/8)*p_{522}^2/\lambda_{LE}$, wherein $n_1$ is a first integer and wherein $\lambda_{LE}$ is a first mean wavelength of said radiation having first mean energy $E_{LE}$.

5. The interferometer device of claim 4, wherein said first integer $n_1$ is an even number.

6. The interferometer device of claim 4, wherein said electromagnetic radiation source is adapted to emit a second mean energy $E_{HE}$ for $\lambda_{HE}$, wherein the mean energy of $E_{HE}$ is a multiplication of $1/q$ with the mean energy $E_{LE}$, and wherein q takes values that range from 0 to 1.

7. The interferometer device of claim 6, wherein the distance between said phase grating and absorption grating is chosen to be a fractional Talbot distance $d_{n2}$, represented by the equation $d_{n2}=(n_2/8)*p_{522}^2/\lambda_{HE}$, wherein $n_2$ is a second integer, and wherein $\lambda_{HE}/\lambda_{LE}=n_1/n_2$.

8. The interferometer device of claim 7, wherein said second integer $n_2$ is an even number.

9. The interferometer device of claim 1, wherein said first aspect ratio of said phase grating is maximal one of the following: 8, 10 and 12.

10. The interferometer device of claim 1, wherein a source grating is positioned between said electromagnetic radiation source and said phase grating, wherein said source grating is adapted to cause spatial coherence on said emitted radiation.

11. A method for performing interferometry, said method comprising:
emitting electromagnetic radiation from the electromagnetic radiation source towards the phase grating having the first aspect ratio;

effecting the phase shift ($\Delta\phi$) on said emitted radiation of $<\pi$ to yield phase-shifted radiation;

absorbing at least some of the phase-shifted radiation emanating from said phase grating by the absorber grating; and detecting radiation emanating from said absorber grating by the detector.

12. The method of claim 11, wherein said radiation is emitted at a first mean energy $E_{LE}$ for $\lambda_{LE}$ and at a second mean energy $E_{HE}$ for $\lambda_{HE}$, wherein the mean energy of $E_{HE}$ is a multiplication of $1/q$ with the mean energy $E_{LE}$, and wherein q takes values that range from 0 to 1, thereby employing a dual-energy scheme.

13. The method of claim 12, wherein distance between said phase grating and said absorption grating is chosen to be a fractional Talbot distance $d_{n2}$, represented by the equation $d_{n2}=(n_2/8)*p_{522}^2/\lambda_{HE}$, wherein $n_2$ is a second integer, and wherein $\lambda_{HE}/\lambda_{LE}=n_1/n_2$.

14. The method of claim 13 wherein said second integer $n_2$ is an even number.

* * * * *

UNITED STATES PATENT AND TRADEMARK OFFICE
CERTIFICATE OF CORRECTION

PATENT NO. : 7,924,973 B2  Page 1 of 1
APPLICATION NO. : 12/269449
DATED : April 12, 2011
INVENTOR(S) : Kottler et al.

It is certified that error appears in the above-identified patent and that said Letters Patent is hereby corrected as shown below:

In column 4, lines 36-37:  amend "X-ray energy, as is schematically illustrated in FIG. 2." to read "X-ray energy."

In column 12, line 25:  add the word "of" after "factor" to read "but stretched by a factor of two"

Signed and Sealed this
Sixteenth Day of August, 2011

David J. Kappos
*Director of the United States Patent and Trademark Office*